US011937782B2

(12) United States Patent
Do

(10) Patent No.: US 11,937,782 B2
(45) Date of Patent: Mar. 26, 2024

(54) ENDOSCOPE CONTROL DEVICE AND ENDOSCOPE COMPRISING AN ENDOSCOPE CONTROL DEVICE

(71) Applicant: HOYA CORPORATION, Tokyo (JP)

(72) Inventor: Anh Minh Do, Friedberg (DE)

(73) Assignee: HOYA CORPORATION, Tokyo (JP)

(*) Notice: Subject to any disclaimer, the term of this patent is extended or adjusted under 35 U.S.C. 154(b) by 297 days.

(21) Appl. No.: 17/284,223

(22) PCT Filed: Oct. 25, 2019

(86) PCT No.: PCT/IB2019/001087
§ 371 (c)(1),
(2) Date: Apr. 9, 2021

(87) PCT Pub. No.: WO2020/089685
PCT Pub. Date: May 7, 2020

(65) Prior Publication Data
US 2022/0022732 A1 Jan. 27, 2022

(30) Foreign Application Priority Data
Oct. 29, 2018 (DE) ..................... 10 2018 126 938.2

(51) Int. Cl.
A61B 1/00 (2006.01)
A61B 1/005 (2006.01)

(52) U.S. Cl.
CPC ........ *A61B 1/0057* (2013.01); *A61B 1/00006* (2013.01); *A61B 1/00098* (2013.01)

(58) Field of Classification Search
CPC .............. A61B 1/0057; A61B 1/00006; A61B 1/00098; A61B 1/005; A61B 1/00; A61B 1/0052; A61B 1/0066
(Continued)

(56) References Cited

U.S. PATENT DOCUMENTS 7,828,724 B2 11/2010 Hosoi et al.
7,846,089 B2 12/2010 Maruyama
(Continued)

FOREIGN PATENT DOCUMENTS

CN 101495045 A 7/2009
CN 101909526 A 12/2010
(Continued)

OTHER PUBLICATIONS

"AMAZON: System-S 1m Meter Mini USB Kabel 90 Grad Links gewinkelt Winkelstecker.Im Angebot von Amazon.de seit: 12", Internet: URL: <https://www.amazon.de/System-S-gewinkelt-Winkelstecker-Datenkabel-Ladekabel/dp/B00ZIFRPJQ>, Jun. 2015, along with an English translation thereof.
(Continued)

Primary Examiner — Timothy J Neal
Assistant Examiner — James Edward Boice
(74) Attorney, Agent, or Firm — GREENBLUM & BERNSTEIN, P.L.C.

(57) ABSTRACT

The invention relates to an endoscope control device including a control body holder, a joystick-like control element for effecting a deflection movement, and at least one control wire guided through the control body holder and transmitting the deflection movement of the control element to an element to be controlled in the endoscope. The control element extends from the control body holder in a proximal direction. The at least one control wire is fixed to the control element in a manner spaced from the control body holder. The control element includes an elastic rod element which is bendable upon actuation of the control element so as to effect a deflection movement.

11 Claims, 4 Drawing Sheets

(58) Field of Classification Search
USPC .......................................................... 600/149
See application file for complete search history.

(56) References Cited

U.S. PATENT DOCUMENTS

| | | | |
|---|---|---|---|
| 8,845,521 B2 | 9/2014 | Maruyama | |
| 2007/0021737 A1 | 1/2007 | Lee et al. | |
| 2008/0015631 A1 | 1/2008 | Lee et al. | |
| 2008/0065116 A1 | 3/2008 | Lee et al. | |
| 2008/0097293 A1* | 4/2008 | Chin ................. | A61M 25/0051 604/524 |
| 2008/0269727 A1 | 10/2008 | Lee et al. | |
| 2009/0023995 A1 | 1/2009 | Lee | |
| 2009/0069842 A1 | 3/2009 | Lee et al. | |
| 2009/0171147 A1* | 7/2009 | Lee ........................ | A61B 17/29 600/137 |
| 2009/0171275 A1 | 7/2009 | Ostrovsky et al. | |
| 2009/0299344 A1 | 12/2009 | Lee et al. | |
| 2012/0143088 A1 | 6/2012 | Schultz | |
| 2012/0302832 A1 | 11/2012 | Inada | |
| 2013/0102846 A1 | 4/2013 | Sjostrom et al. | |
| 2015/0105625 A1 | 4/2015 | Lee | |
| 2015/0196364 A1 | 7/2015 | Perez, III et al. | |
| 2016/0354114 A1 | 12/2016 | Lee | |
| 2017/0196546 A1 | 6/2017 | Lee | |
| 2019/0125469 A1* | 5/2019 | Yang ........................ | A61M 5/14 |
| 2019/0380560 A1 | 12/2019 | Shijo | |

FOREIGN PATENT DOCUMENTS

| | | |
|---|---|---|
| CN | 102711629 A | 10/2012 |
| JP | 2010-503457 A | 2/2010 |
| JP | 2010-538738 A | 12/2010 |
| JP | 2012-525916 A | 10/2012 |
| JP | 2016-221024 A | 12/2016 |
| JP | 2016221024 A | 12/2016 |
| WO | WO 2010/129035 A2 | 11/2010 |
| WO | WO 2008/033240 A2 | 3/2018 |
| WO | WO2009/035508 A1 | 3/2019 |

OTHER PUBLICATIONS

U.S. Appl. No. 17/281,429 to Anh Minh Do, which was filed on Mar. 30, 2021.

Written Opinion of the International Searching Authority issued in International Bureau of Wipo Patent Application No. PCT/IB2019/001087, dated Feb. 4, 2020, along with an English translation thereof.

German Search Report issued in GERMAN Patent Application No. 10 2018 126 938.2.

International Search Report issued in International Bureau of WIPO Patent Application No. PCT/IB2019/001087, dated Feb. 4, 2020, along with an English translation thereof.

Japanese Office Action issued in Japanese Patent Application No. 2021-523457, dated Sep. 12, 202, together with an English-language translation.

European Office Action issued in EPO Application No. 19797362.1, dated June 28, 2023.

Chinese Office Action issued in Chinese Patent Application No. 201980071573.4, dated May 22, 2023.

* cited by examiner

ENDOSCOPE CONTROL DEVICE AND ENDOSCOPE COMPRISING AN ENDOSCOPE CONTROL DEVICE

The present invention relates to an endoscope control device comprising a control body holder and a joystick-like control element for effecting a deflection movement. The present invention further relates to an endoscope comprising such an endoscope control device.

In a known endoscope, an endoscope control device effecting a deflection movement is provided on a proximal side. Usually, a deflection movement of a pivoting element arranged on a distal side is realized thereby.

For example, the US 2012/0302832 A1 discloses an endoscope comprising an endoscope control device in which a joystick is pivoted about a pivot point. A plate-like arm extends from the joystick, with pulling cables being anchored to the arm at a distance from the joystick. The pulling cables extend from a control body holder to a distal portion of the endoscope and are anchored to a swing-out element. The joystick pivots relative to the control body holder. In this way, the pivoting movement of the swing-out element arranged on the distal side is realized.

In an endoscope head, there is always a need to save space in order to advantageously accommodate the required components in a small space.

Thus, it is the object of the invention to provide an improved endoscope control device in which as few components as necessary are arranged in a space-saving way. Advantageously, the endoscope control device should be simple in design and incur the lowest possible production costs.

This object is achieved by an endoscope control device comprising the features of claim 1.

Advantageous developments are the subject matter of the dependent claims.

Thus, the invention relates to an endoscope control device comprising a control body holder, a joystick-like control element for effecting a deflection movement, and at least one control wire guided through the control body holder and transmitting the deflection movement of the control element to an element to be controlled in the endoscope. The control element extends from the control body holder in a proximal direction, and the at least one control wire is fixed to the control element in a manner spaced from the control body holder. The control element comprises an elastic rod element which is bendable upon actuation of the control element so as to effect a deflection movement. Since the deflection movement is realized by a mere bending (kinking) of the elastic rod element, the endoscope control device can be constructed with very few components in a simple, space-saving and cost-effective manner. A large number of additional components is avoided.

The control element can have an actuating portion on the side opposite to the control body holder, wherein, when the control element is actuated to tension the at least one control wire, the rod element is bent.

The actuating portion can be formed as a cover element and can cover the proximal end of the rod element, with the at least one control wire being clamped between the rod element and the cover element.

The rod element can comprise a predefined target bending position.

The endoscope control device can further comprise two interlocking hemispherical bearing shells, the first bearing shell of which is supported on the control body holder and the second bearing shell of which is supported on the proximal end of the rod element, the two bearing shells surrounding the elastic rod element. The two bearing shells guide the bending movement of the elastic rod element. Thus, bending of the elastic rod element can be performed in a stable manner and in accordance with the desired deflection intention.

Centrally along its longitudinal extension on the outer circumference, the elastic rod element can have parallel discs extending outwards in the radial direction, wherein, seen in the longitudinal direction of the rod element, the spaces between the discs are provided in the number of the control wires, wherein the discs have guide openings on the outer circumferential edge for guiding a control wire, the guide openings for the same control wire being aligned in the longitudinal direction of the rod element, and the guide openings for different control wires being offset from each other in the circumferential direction of the rod element.

In the area of the outer circumferential edge, adjacent discs can be connected by bridging portions, wherein each bridging portion is formed at adjacent discs such that circumferential edge portions of the adjacent discs are bendable toward each other on the side diametrically opposite to the bridging portion, and wherein the bridging portions are arranged offset from disc to disc in the circumferential direction.

The number of the control wires may be four. Alternatively, the number of the control wires is not limited. If four control wires are used, the four control wires can be combined into two pairs of control wires facing each other relative to the rod element, with the ends of each pair being connected. This keeps the number of control wires to a minimum, while still allowing a deflection movement in all directions.

The elastic rod element can be displaceable relative to the control body holder. Alternatively, the elastic rod element can be fixedly arranged on the control body holder.

The elastic rod element can be made of plastic or metal.

The invention further relates to an endoscope comprising such an endoscope control device. The invention can be applied to any kind of endoscope in which a deflection movement is controlled by a control element.

The aspects of the present invention explained above can be combined in a suitable manner.

Figure 1:
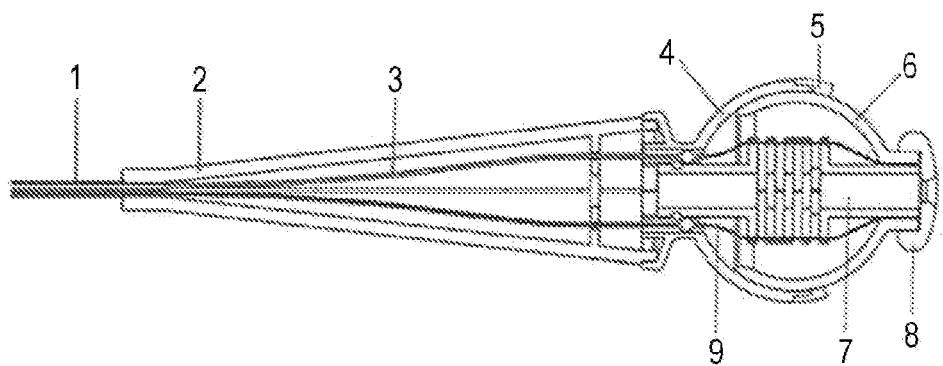
FIG. 1 shows a schematic side section view of an endoscope control device according to a first embodiment of the present invention.

In the following, the present invention is described in detail while referring to the drawings by means of embodiments.

FIRST EMBODIMENT

In the following, a first embodiment of the present invention is described while referring to FIGS. 1 to 7.

Figure 2:
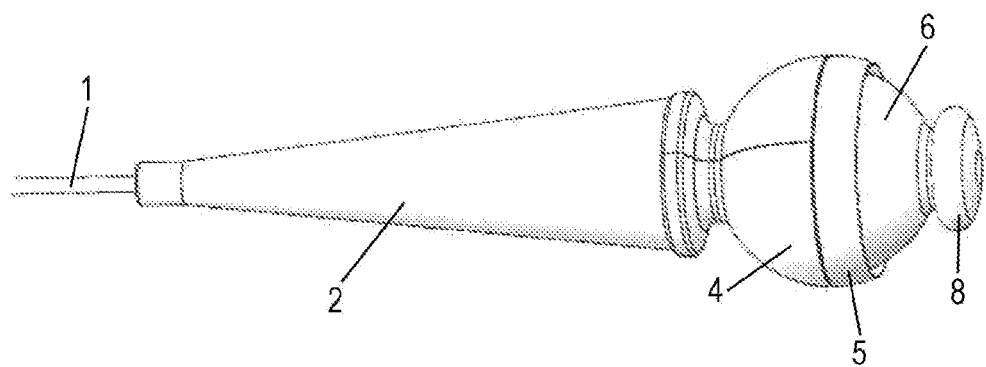
FIG. 2 shows a schematic perspective view of the endoscope control device according to the first embodiment.

FIG. 1 shows a schematic side section view of an endoscope control device of the first embodiment. FIG. 2 shows a schematic perspective view of this endoscope control device.

The endoscope control device constitutes a proximal portion of an endoscope. The endoscope has an elastic insertion tube 1 which extends distally from a control body housing 2. The insertion tube 1 is inserted into a hollow space of a patient. On the distal side (not shown), the insertion tube 1 has a bendable portion, i.e. a so-called deflecting portion which can be pivoted relative to the proximal part of the insertion tube 1. The pivoting movement of the deflecting portion is controlled by pivoting a control element to be explained below, with the movement of the deflecting portion exactly following the movement of the control element.

For the purpose of the transmission of the pivoting movement from the control element to the deflecting portion, four control wires 9 extend as pulling cables (pulling wires) from the control body housing 2 in the insertion tube 1 to the deflecting portion. In the deflecting portion, the control wires 9 are anchored in a known manner offset at the circumference at equal intervals. Therefore, the anchoring locations of the control wires 9 at the deflecting portion are each offset from each other by 90 degrees. By pulling a control wire 9, the deflecting portion is pivoted to the side on which the anchoring location of the pulled control wire 9 is provided. The control wires 9 are guided in a known manner in respective flexible guide springs 3 in the insertion tube 1. The guide springs 3 extend from the proximal end of the deflecting portion in the insertion tube 1 in the proximal direction into the control body housing 2. The respective guide spring 3 acts as a Bowden cable sheath for the control wire 9 assigned to it.

The control body housing 2 is made of plastic. The control body housing 2 is designed in the shape of a cylinder whose diameter gradually increases towards the proximal side. The control body housing 2 has a central axis. On the distal side of the control body housing 2, the insertion tube 1 extends in the distal direction. The insertion tube 1 is located in the control body housing 2. The insertion tube 1 does not move relative to the control body housing 2. The shape of the control body housing 2 is not limited. Other shapes may be used.

On its proximal side, the control body housing 2 has a port to which a first bearing shell 4 is fixedly attached. The first bearing shell 4 forms a hemispherical bearing in the shape of a hemisphere open to the proximal side.

More specifically, as shown in FIG. 2, the first bearing shell 4 is constructed in the shape of an egg cup. The side of the egg cup stand forms the distal side of the first bearing shell 4 and is attached to the control body housing 2. The proximal side forms a bearing shell body of the first bearing shell 4. The first bearing shell 4 may be manufactured such that two symmetrical egg cup halves are glued together. However, the manufacture is not limited to this. On the distal side of the first bearing shell 4, an annular element 5 is arranged. Moreover, on the distal inner circumferential side, the first bearing shell 4 is formed in a cylindrical shape of constant diameter.

The first bearing shell 4 and the annular element 5 hold a second bearing shell 6. The second bearing shell 6 forms a hemispherical body to be supported, which is in the shape of a hemisphere open to the distal side. Here, the first bearing shell 4 acts as a first housing element and the annular element 5 acts as a second housing element to accommodate the second bearing shell 6.

The first bearing shell 4 and the annular element 5 are spherical at least on their inner surface. The second bearing shell 6 is spherical at least on its outer surface. The spherical shape of the second bearing shell 6 and the spherical shape of the bearing shell body of the first bearing shell 4 and the annular element 5 are selected such that the second bearing shell 6 can move in the first bearing shell 4 and in the annular element 5 relative to the first bearing shell 4 and the annular element 5. Here, the distal side of the second bearing shell 6 is located in the proximal side, i.e. in the bearing shell body of the first bearing shell 4.

The annular element 5 prevents the second bearing shell 6 from escaping from the first bearing shell 4 in the distal direction.

The first bearing shell 4, the annular element 5 and the second bearing shell 6 are made of plastic.

On the proximal side of the second bearing shell 6, the tapering spherical shape changes into a cylindrical shape of constant diameter. The cylindrical shape of constant diameter of the second bearing shell 6 extends in the proximal direction.

The diameter of the cylinder portion formed on the proximal side of the second bearing shell 6 equals the diameter of the cylinder portion formed on the distal side of the first bearing shell 4 on the inner circumference.

A rod element 7 extends between the cylinder portion formed on the distal side of the first bearing shell 4 on the inner circumference and the cylinder portion formed on the proximal side of the second bearing shell 6. The rod element 7 acts as a control element or control body within the meaning of the invention.

Thus, the control body housing 2 acts as a control body holder.

The rod element 7 is a tubular element. The rod element 7 is made of an elastic material such as plastic or metal. The rod element 7 extends on the extended center axis of the control body housing 2. The rod element 7 has a distal tube portion 7A on the distal side and a proximal tube portion 7B on the proximal side.

The distal side of the rod element 7 is held by an inner circumferential portion (of the egg cup stand) of the first bearing shell 4. The inner circumferential portion of the first bearing shell 4 prevents the distal tube portion 7A from moving radially. The inner circumferential portion of the first bearing shell 4 additionally prevents the distal tube portion 7A from moving in the longitudinal direction.

On the outer circumference of the distal tube portion 7A, respective guide spring holders 31 for the four guide springs 3 are arranged in a fixed position. Thus, four respective guide spring holders 31 are provided.

The guide spring holder 31 acts as a pull counter holder. The guide spring holder 31 takes up (receives) the proximal end of the guide spring 3 and discharges the compressive force resulting from the guide spring 3 into the rod element 7. On the proximal side of the guide spring holder 31, the control wire 9 therefore emerges from its guide spring 3 and extends in the proximal direction.

The respective guide spring holders 31 are arranged between the inner circumferential portion of the first bearing shell 4 and the distal tube portion 7A such that no relative displacement is possible therebetween.

The proximal side of the rod element 7 is held by an inner circumferential portion of the second bearing shell 6. In other words, the inner circumferential portion of the second bearing shell 6 prevents the proximal tube portion 7B from moving radially. Furthermore, a cover element 8, which is also a part of the control element, is located on the proximal side of the proximal tube portion 7B and the second bearing shell 6. The cover element 8 covers the proximal side of the proximal tube portion 7B and the second bearing shell 6. The cover element 8 prevents the proximal tube portion 7B from moving in the longitudinal direction relative to the inner circumferential portion of the second bearing shell 6.

Thus, a relative movement of the proximal tube portion 7B to the distal tube portion 7A is guided by the first bearing shell 4 and the second bearing shell 6. The second bearing shell 6 and the cover element 8 form a joystick head.

In this context, the proximal ends of the control wires 9 are clamped between the inner circumferential portion of the second bearing shell 6 and the proximal tube portion 7B. At the proximal end of the proximal tube portion 7B, the control wires 9 are bent inwards and are clamped by the cover element 8. Thus, the cover element 8 makes sure that a relative movement of the control wires 9 to the proximal end portion of the proximal tube portion 7B is prevented.

The course of the control wires 9 in this case is such that two control wires 9 facing each other with respect to the diameter of the proximal tube portion 7B always form a pair. Thus, when considering FIG. 3, a front control wire 9 and a rear control wire 9 form a pair, and an upper control wire 9 and a lower control wire 9 form a pair. On the distal side, the control wires 9 forming a pair are connected at the deflecting portion. On the proximal side, the control wires 9 forming a pair are connected (e.g. by knotting, welding, etc.). The proximal end portion of each control wire 9 thus passes into the proximal end portion of the associated control wire 9 with which it forms a pair. Hence, strictly speaking, two pairs of control wires 9 are used in the embodiment.

Between the distal tube portion 7A and the proximal tube portion 7B, the rod element 7 has an integral disc element that will be described in the following.

The disc element is integrally embedded between the distal tube portion 7A and the proximal tube portion 7B.

The disc element is formed as a cylindrical body which has an outer diameter larger than the distal tube portion 7A and the proximal tube portion 7B. The disc element is made up of five successive discs 71, 72, 73, 74, 75 of the same thickness, viewed in the axial direction. In the longitudinal direction, the successive discs 71, 72, 73, 74, 75 are equally spaced with respect to each other. Thus, the discs 71, 72, 73, 74, 75 have (inter)spaces with the same longitudinal dimension each. Respectively two adjacent discs are connected on the outer circumference by a bridging portion 76, 77, 78, 79. From disc to disc, the bridging portion is offset in the circumferential direction by, for example, a quarter of the total circumference. The discs 71, 72, 73, 74, 75 are parallel to each other.

More specifically, the first disc 71 and the second disc 72 are connected on the outer circumference by a first bridging portion 76. The second disc 72 and the third disc 73 are connected on the outer circumference by a second bridging portion 77. The third disc 73 and the fourth disc 74 are connected on the outer circumference by a third bridging portion 78. The fourth disc 74 and the fifth disc 75 are connected on the outer circumference by a fourth bridging portion 79.

The first bridging portion 76 is offset from the second bridging portion 77 in the circumferential direction of the disc element. The second bridging portion 77 is offset from the third bridging portion 78 in the circumferential direction of the disc element. The third bridging portion 78 is offset from the second bridging portion 77 in the circumferential direction of the disc element. The fourth bridging portion 79 is offset from the third bridging portion 78 in the circumferential direction of the disc element.

Figure 7:
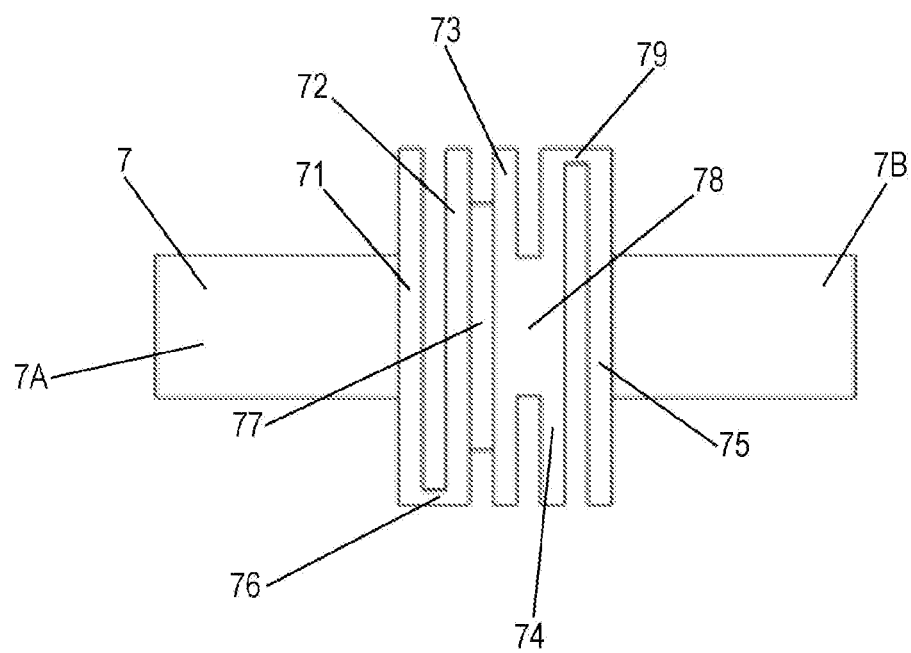
FIG. 7 shows a schematic side view of the elastic rod element of the endoscope control device according to the first embodiment.

The disc element is manufactured, for example, by cutting the spaces between the discs 71, 72, 73, 74, 75, e.g. by laser, in such a way that only the small bridging portion 76, 77, 78, 79 remains at the edge, see FIG. 7.

More specifically, a space between the discs 71 and 72 is cut by laser in such a way that a small bridging portion 76 remains at the edge. Then the disc element is rotated by 90 degrees and the next space between the discs 72 and 73 is cut in such a way that a small bridging portion 77 remains at the edge. Then the disc element is further rotated by 180 degrees and the next space between the discs 73 and 74 is cut in such a way that a small bridging portion 78 remains at the edge. Then the disc element is further rotated by 90 degrees and the next space between the discs 74 and 75 is cut in such a way that a small bridging portion 79 remains at the edge.

Figure 3:
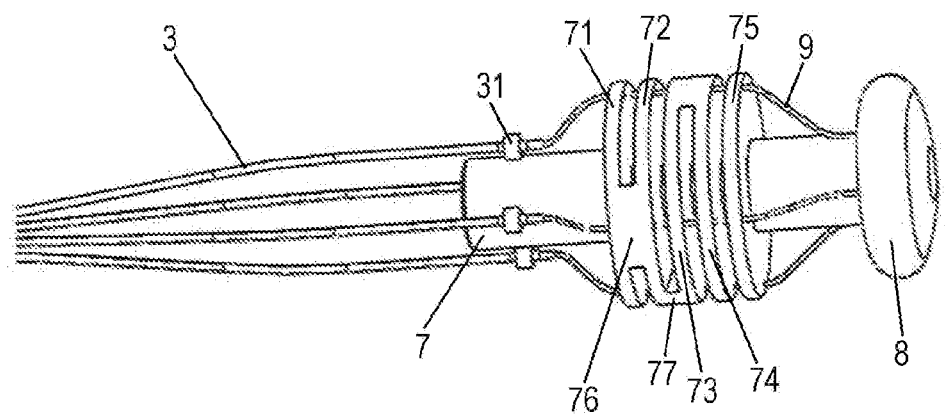
FIG. 3 shows a schematic perspective view of a control element comprising a disc element of the endoscope control device according to the first embodiment.
Figure 4:
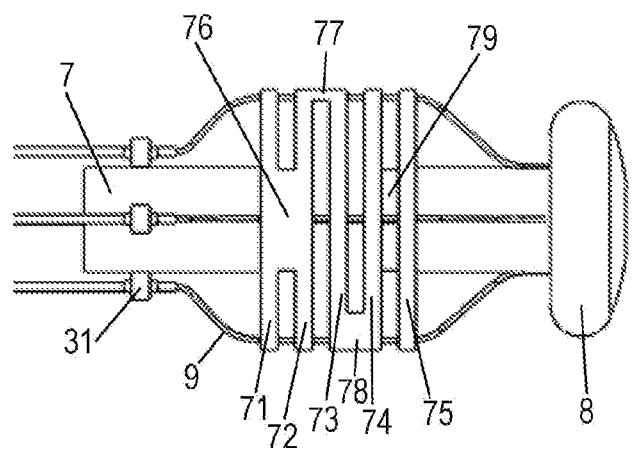
FIG. 4 shows a schematic side view of the control element of the endoscope control device according to the first embodiment.
Figure 5:
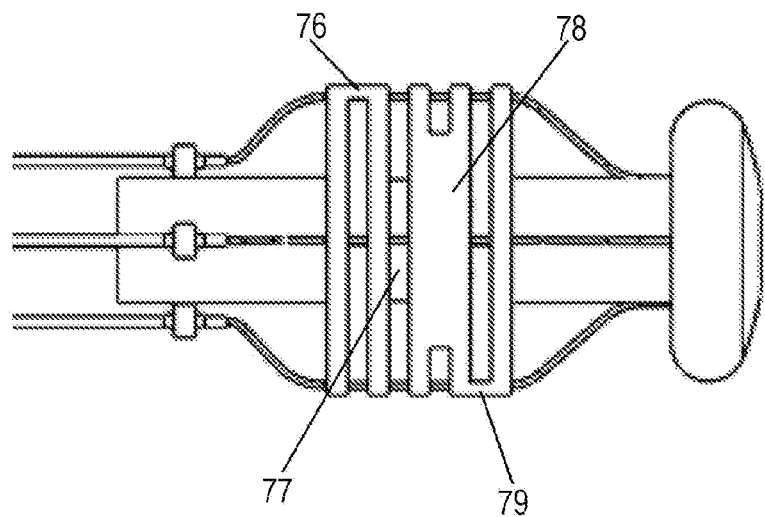
FIG. 5 shows a further schematic side view of the control element of the endoscope control device according to the first embodiment, wherein in particular bridging portions at the disc element are shown.

Thus, the proximal tube portion 7B is kinkable relative to the distal tube portion 7A by bending the proximal tube portion 7B in the direction which is diametrically opposite to a respective bridging portion 76, 77, 78, 79. In FIG. 3, for example, the bridging portion 76 faces the viewer. By pushing the proximal tube portion 7B in the illustration of FIG. 3 away from the viewer, the part of the rod element 7 proximal to the bridging portion 76 bends (kinks) relative to the distal tube portion 7A, with the bridging portion 76 serving as a rotation area (pivot point) until the outer circumferential portion of the first disc 71 opposite to the bridging portion 76 abuts on the outer circumferential portion of the second disc 72 opposite to the bridging portion 76.

Similarly, the proximal tube portion 7B can be bent relative to the distal tube portion 7A by respectively pushing the proximal tube portion 7B laterally of the bridging portion 77, 78 or 79 such that the bridging portion 77, 78 or 79 serves as a pivot point respectively.

Figure 6:
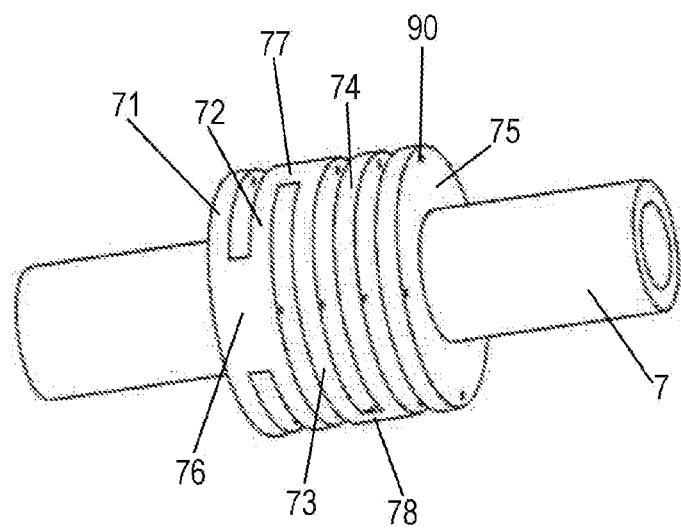
FIG. 6 shows a schematic perspective view of an elastic rod element of the endoscope control device according to the first embodiment, without pulling cables.

In the disc element, four openings 90 extending in the longitudinal direction of the disc element are provided such that they pass through each disc 71, 72, 73, 74, 75, see FIG. 6. These openings 90 are guide openings for the respective control wires 9. The four openings 90 extending in the longitudinal direction of the disc element are also offset from each other by, for example, a quarter of the total circumference of the disc element.

Thus, each bridging portion 76, 77, 78, 79 has a portion through which an opening 90 extends, see FIG. 3. It can be seen from FIG. 3 that the first bridging portion 76 has an opening 90 for the front control wire 9. The second bridging portion 77 has an opening 90 for the lower control wire 9 in FIG. 3. The third bridging portion 78 has an opening 90 for the upper control wire 9. The fourth bridging portion 79 has an opening 90 for the rear control wire 9.

Hence, the disc element ensures that, when the rod element 7 is actuated (bent), a predefined target bending position is provided for each control wire 9 in the rod element 7.

For example, in the illustration of FIG. 3, when the proximal tube portion 7B is pushed away from the viewer, the proximal tube portion 7B bends relative to the distal tube portion 7A, with the bridging portion 76 serving as a rotation area (pivot point). Thus, the front control wire 9 is tensioned (pulled) and the rear control wire 9 is relaxed. The pair of the front control wire 9 and the rear control wire 9 thus ensures a deflection movement on the distal side of the endoscope, which corresponds to the pushing movement at the proximal tube portion 7B.

In the embodiment, this pushing movement at the proximal tube portion 7B takes place at the cover element 8 and is guided by the bearing shells 4 and 6.

In this way, a deflection movement at the distal deflecting portion is enabled in the embodiment by a simple and inexpensively manufacturable construction consisting of few individual parts.

ALTERNATIVES AND FURTHER EMBODIMENTS

The explained embodiments can be suitably combined, provided that this does not result in any technical contradiction.

In the embodiment, the distal side of the rod element 7 is held by the inner circumferential portion of the first bearing shell 4. This means that the inner circumferential portion of the first bearing shell 4 prevents the distal tube portion 7A from moving radially and in the longitudinal direction. In an alternative, the distal side of the rod element 7 is held by the inner circumferential portion of the first bearing shell 4 such that the distal tube portion 7A cannot move radially but can move in the longitudinal direction. Thus, a slight displacement of the rod element 7 relative to the inner circumferential portion of the first bearing shell 4 is possible in the longitudinal direction of the rod element 7. In this example, the elastic rod element 7 is displaceable relative to the control body holder 2 in the longitudinal direction, i.e. the axial direction.

The respective guide spring holders 31 can be fixedly anchored at the inner circumferential portion of the first bearing shell 4 or at the distal tube portion 7A. For example, the guide spring holders 31 can be glued to the inner circumferential portion of the first bearing shell 4 or to the distal tube portion 7A.

In the embodiment, the control wires 9 forming a pair are connected on the proximal side. The control wires 9 forming a pair are also connected on the distal side.

Alternatively, the control wires 9 can be used as four completely separate control wires 9.

In the embodiment, the bridging portion at the disc element is offset from disc to disc in the circumferential direction by a quarter of the total circumference (90 degrees). The invention is not limited to this. The amount of offset of the bridging portion from disc to disc may be larger or smaller. The amount of offset of the bridging portion from disc to disc may even be different from each other. The principle of the invention is already realized when a bridging portion between two discs is assigned to each pulling wire.

LIST OF REFERENCE SIGNS

1 Insertion tube of the endoscope
2 control body housing; control body holder
3 guide spring of the pulling cables
4 hemispherical bearing; first bearing shell
5 annular element
6 joystick head; second bearing shell
7 elastic rod element; control element
8 cover element; control element
9 control wire; pulling cable
31 guide spring holder
70 disc element
71 first disc
72 second disc
73 third disc
74 fourth disc
75 fifth disc
76 bridging portion
77 bridging portion
78 bridging portion
79 bridging portion
90 guide openings

The invention claimed is:

1. An endoscope control device comprising
a control body holder,
a joystick-like control element for effecting a deflection movement, and
at least one control wire guided through the control body holder and transmitting the deflection movement of the control element to an element to be controlled in the endoscope, wherein:
the control element extends from the control body holder in a proximal direction, and the at least one control wire is fixed to the control element in a manner spaced from the control body holder,
the control element comprises an elastic rod element which is bendable upon actuation of the control element so as to effect a deflection movement,
centrally along the longitudinal extension on the outer circumference of the elastic rod element, the elastic rod element has parallel discs extending outwards in the radial direction,
in the area of the outer circumferential edge of the elastic rod, adjacent discs are connected by bridging portions,
each bridging portion is formed at adjacent discs such that circumferential edge portions of the adjacent discs are bendable toward each other on the side diametrically opposite to the bridging portion, and
the bridging portions are arranged offset from disc to disc by 90 degrees in the circumferential direction.

2. The endoscope control device according to claim 1, wherein
the control element has an actuating portion on the side opposite to the control body holder, and
wherein, when the control element is actuated to tension the at least one control wire, the rod element is bent.

3. The endoscope control device according to claim 2, wherein
the actuating portion comprises a cover element which covers the proximal end of the rod element, with the at least one control wire being clamped between the rod element and the cover element.

4. The endoscope control device according to claim 1, wherein
the rod element comprises a predefined target bending position.

5. The endoscope control device according to claim 1, wherein
the endoscope control device further comprises two interlocking hemispherical bearing shells, a first bearing shell of which is supported on the control body holder and a second bearing shell of which is supported on the proximal end of the rod element, the two bearing shells surrounding the elastic rod element.

6. The endoscope control device according to claim 1, wherein in the longitudinal direction of the rod element, a number of spaces between the discs is equal to a number of the control wires, the discs have guide openings on the outer circumferential edge for guiding a control wire, and the guide openings or the same control wire are aligned in the longitudinal direction of the rod element, and the guide openings for different control wires are offset from each other in the circumferential direction of the rod element.

7. The endoscope control device according to claim 1, wherein the number of the control wires is four.

8. The endoscope control device according to claim 1, wherein the elastic rod element is displaceable relative to the control body holder.

9. The endoscope control device according to claim 1, wherein the elastic rod element is fixedly arranged on the control body holder.

10. The endoscope control device according to claim 1, wherein the elastic rod element is made of plastic or metal.

11. The endoscope comprising an endoscope control device according to claim 1.

* * * * *